(12) United States Patent
Staylor et al.

(10) Patent No.: US 6,585,685 B2
(45) Date of Patent: Jul. 1, 2003

(54) JET INJECTOR APPARATUS AND METHOD

(75) Inventors: John Lawrence Staylor, Wilsonville, OR (US); Sergio Landau, Laguna Nigel, CA (US); Daniel E. Williamson, Sherwood, OR (US)

(73) Assignee: Bioject Inc., Portland, OR (US)

( * ) Notice: Subject to any disclaimer, the term of this patent is extended or adjusted under 35 U.S.C. 154(b) by 0 days.

(21) Appl. No.: 10/143,475

(22) Filed: May 9, 2002

(65) Prior Publication Data

US 2002/0188251 A1 Dec. 12, 2002

Related U.S. Application Data

(63) Continuation-in-part of application No. 10/057,052, filed on Jan. 25, 2002, and a continuation-in-part of application No. 09/877,911, filed on Jun. 8, 2001.

(51) Int. Cl.[7] .................................................. A61M 5/30
(52) U.S. Cl. ......................... 604/68; 604/70; 604/136; 604/181
(58) Field of Search .............................. 604/68–72, 136, 604/140–145, 181–187, 207–211, 246

(56) References Cited

U.S. PATENT DOCUMENTS

| | | | | |
|---|---|---|---|---|
| 4,913,699 A | * | 4/1990 | Parsons | 604/68 |
| 5,503,627 A | * | 4/1996 | McKinnon et al. | 604/68 |
| 5,704,911 A | * | 1/1998 | Parsons | 604/72 |
| 6,096,002 A | * | 8/2000 | Landau | 604/143 |
| 6,387,074 B1 | * | 5/2002 | Horppu et al. | 604/89 |

* cited by examiner

Primary Examiner—Robert M. Fetsuga
Assistant Examiner—Amanda R. Flynn
(74) Attorney, Agent, or Firm—Kolisch Hartwell, P.C.

(57) ABSTRACT

A gas-powered, durable, needle-free hypodermic jet injection device includes a hand-held injector which carries a disposable injection cartridge with a volume of liquid medication to be injected in the form of a high velocity jet capable of penetrating the skin without the use of a hypodermic needle. The injection device provides an injection orifice, and an injection piston. Forceful movement of the injection piston caused by high pressure gas causes a high velocity injection jet of liquid medication to be expelled from the injection cylinder via the injection orifice. The injection device includes features which improve its safety, and also which improve its ease of manufacture, its durability, and its cost effectiveness.

26 Claims, 12 Drawing Sheets

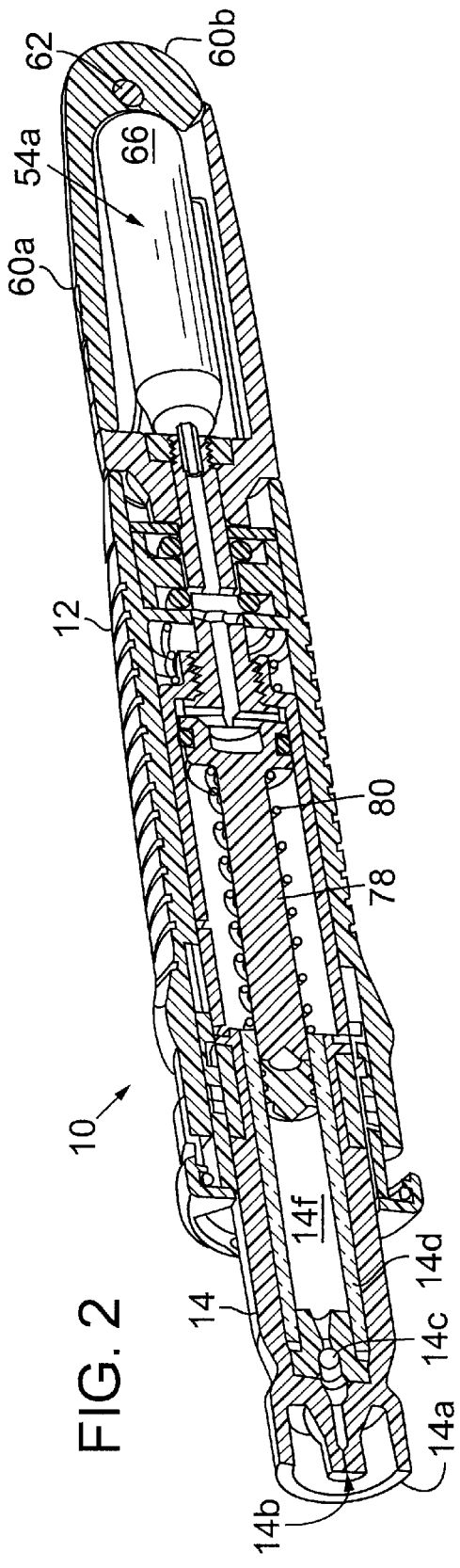
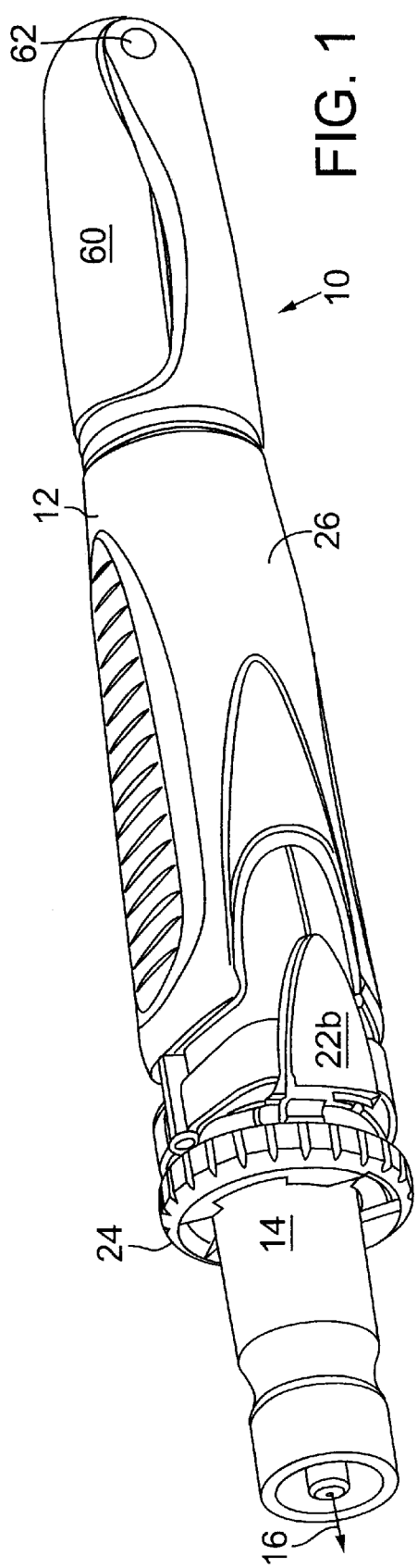

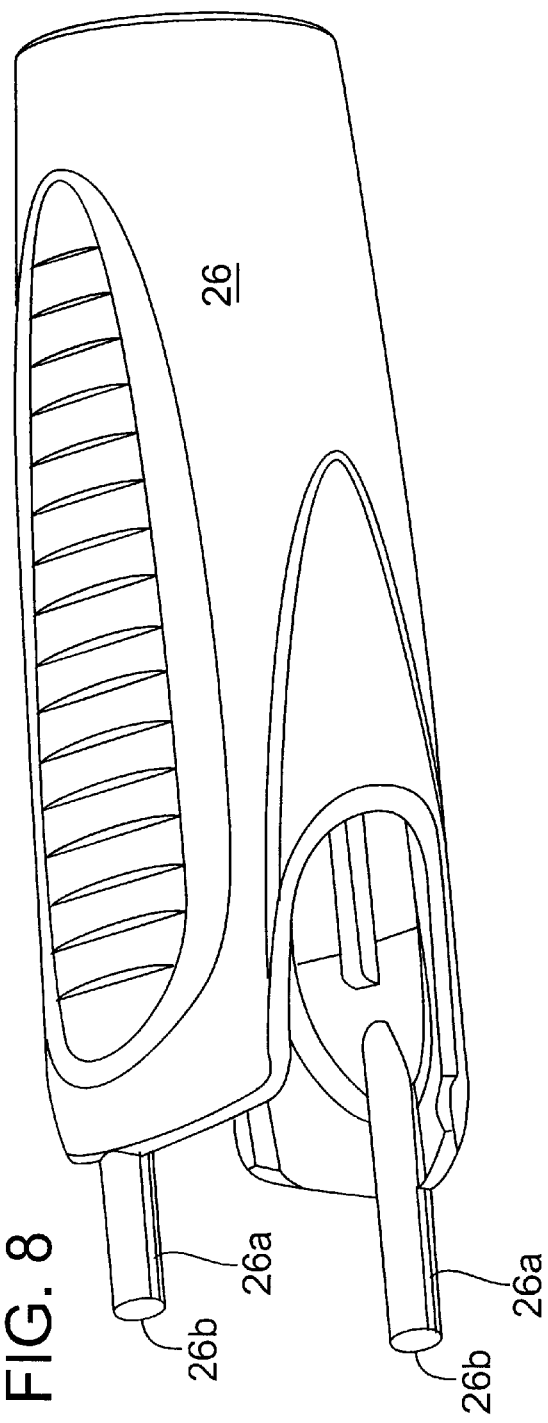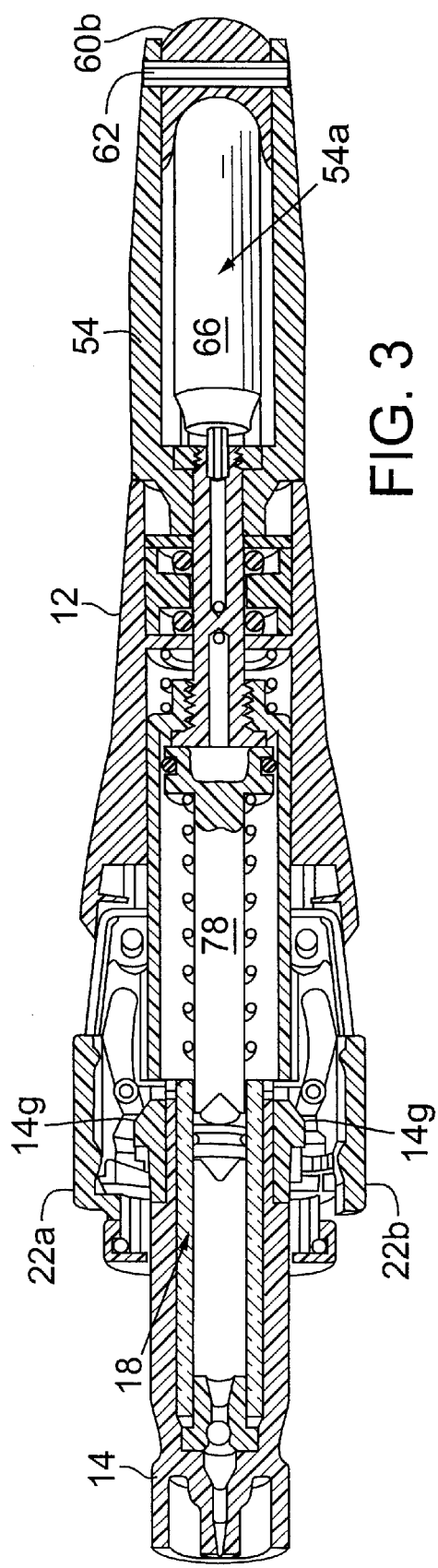

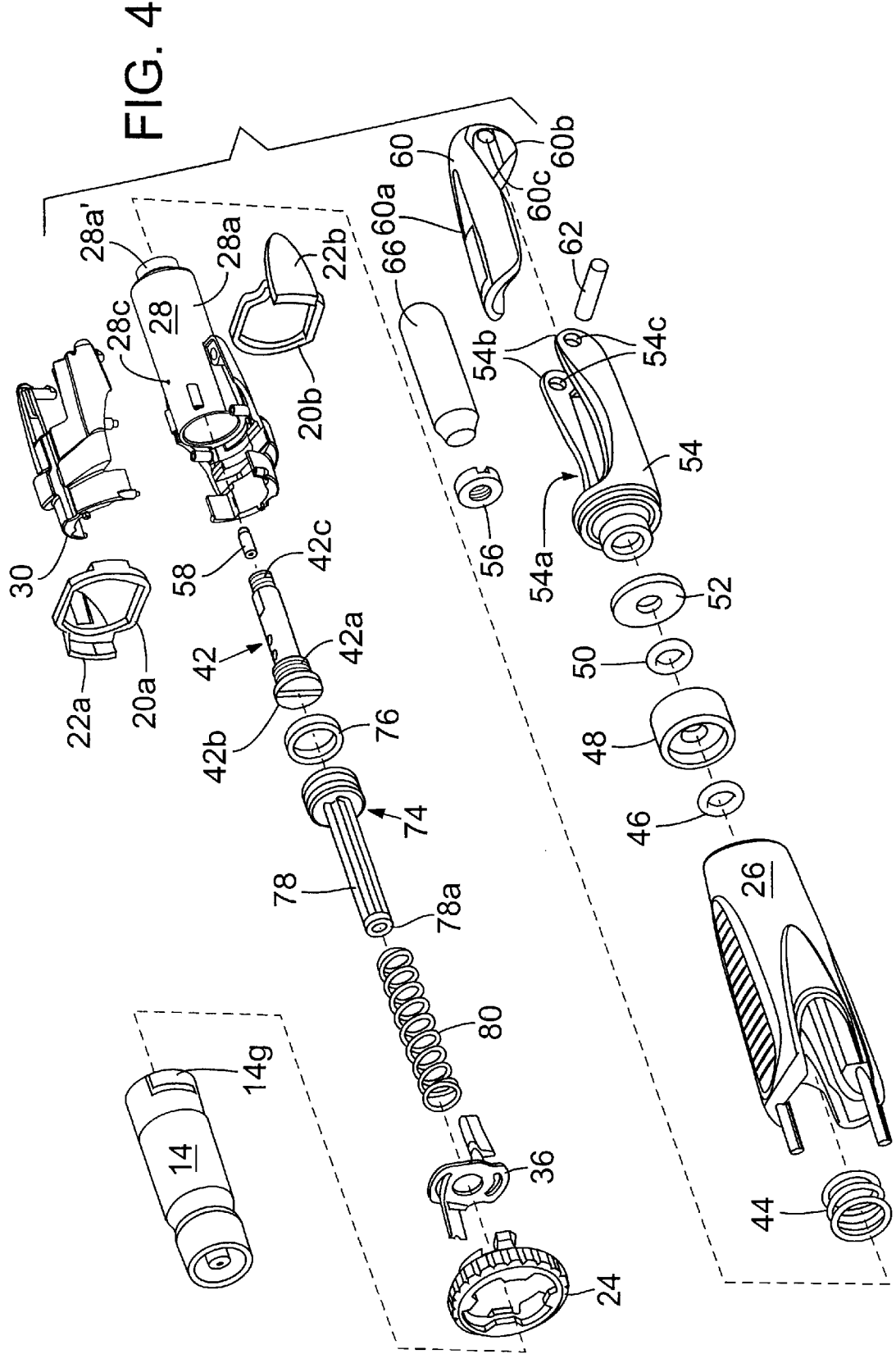

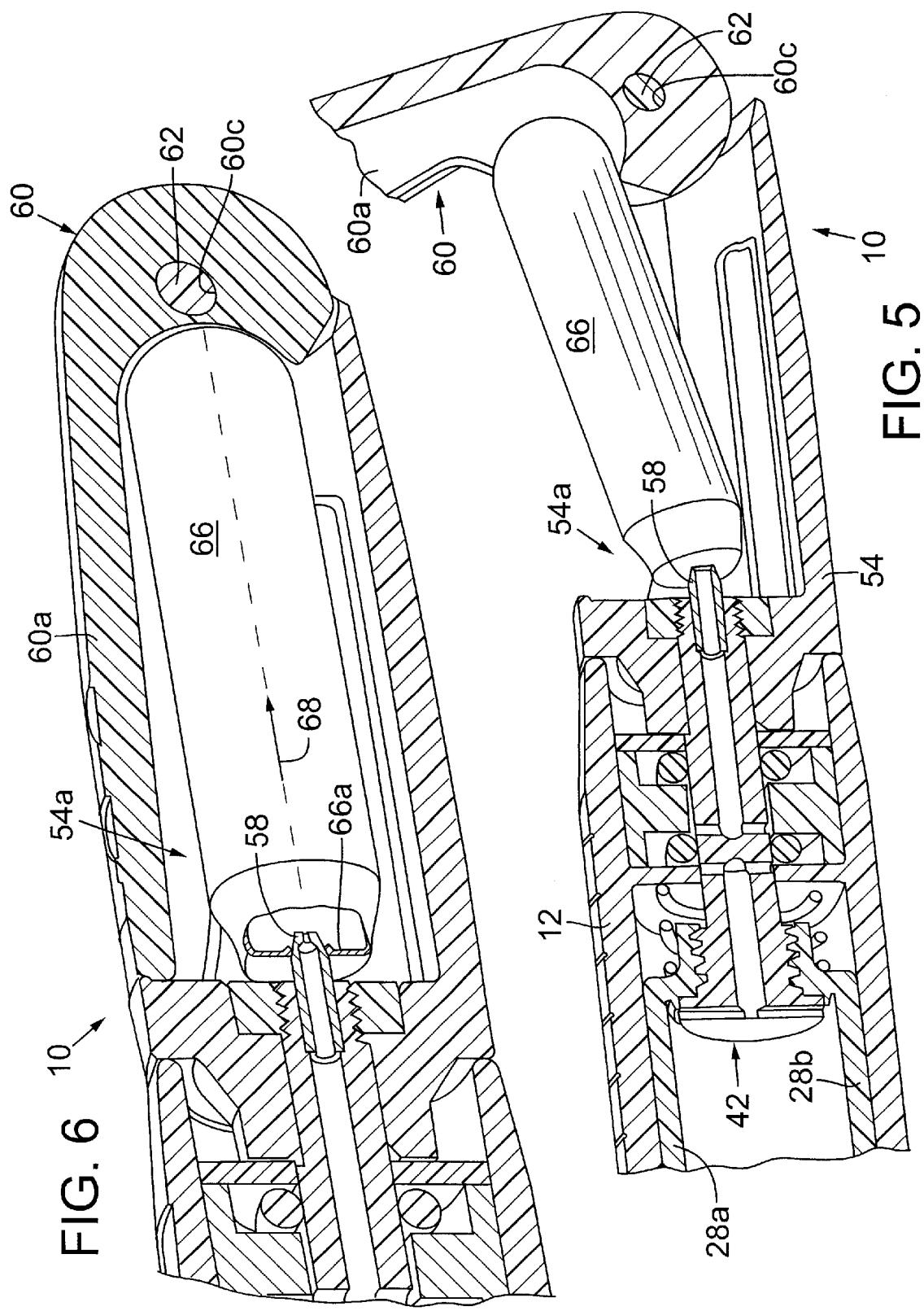

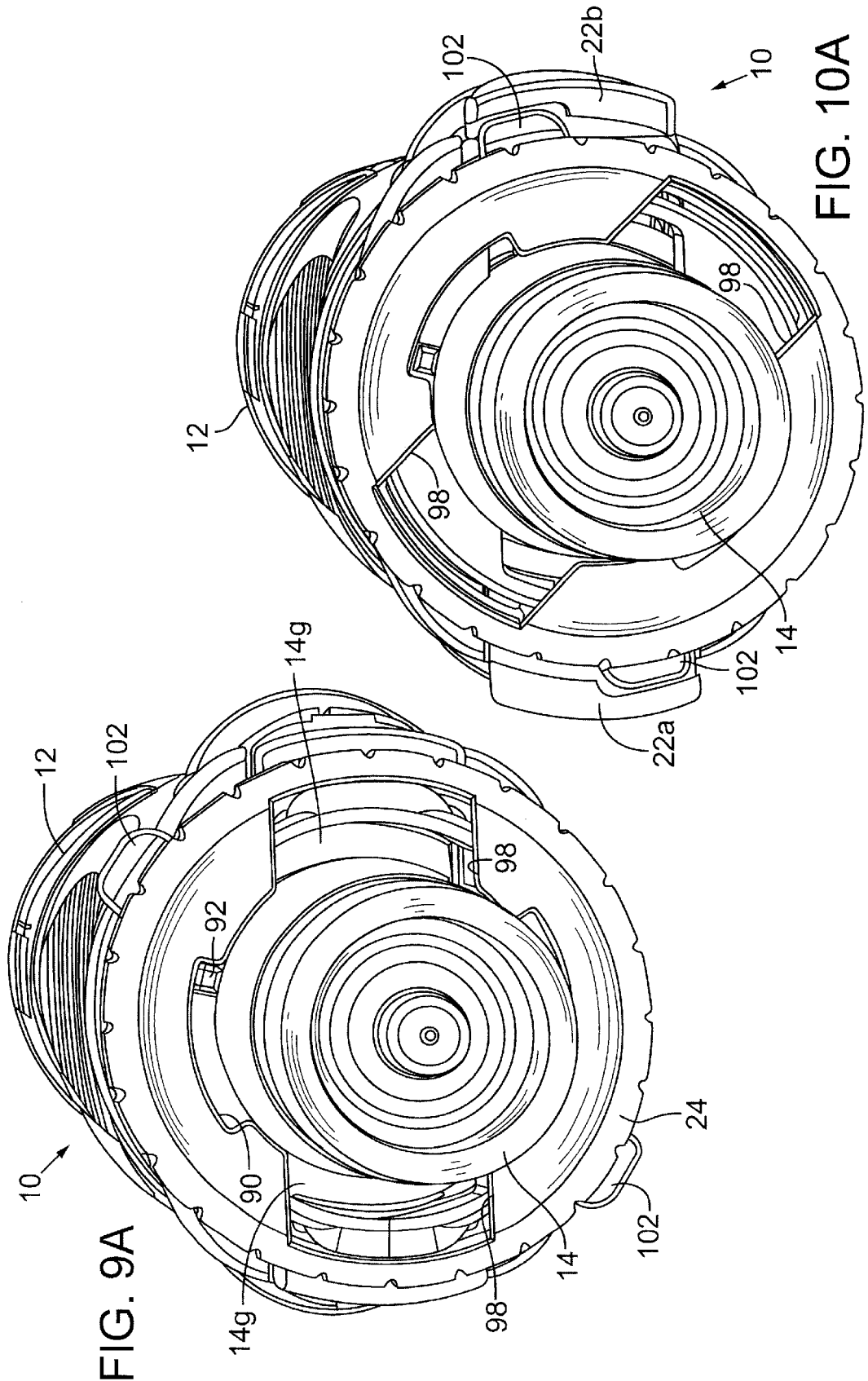

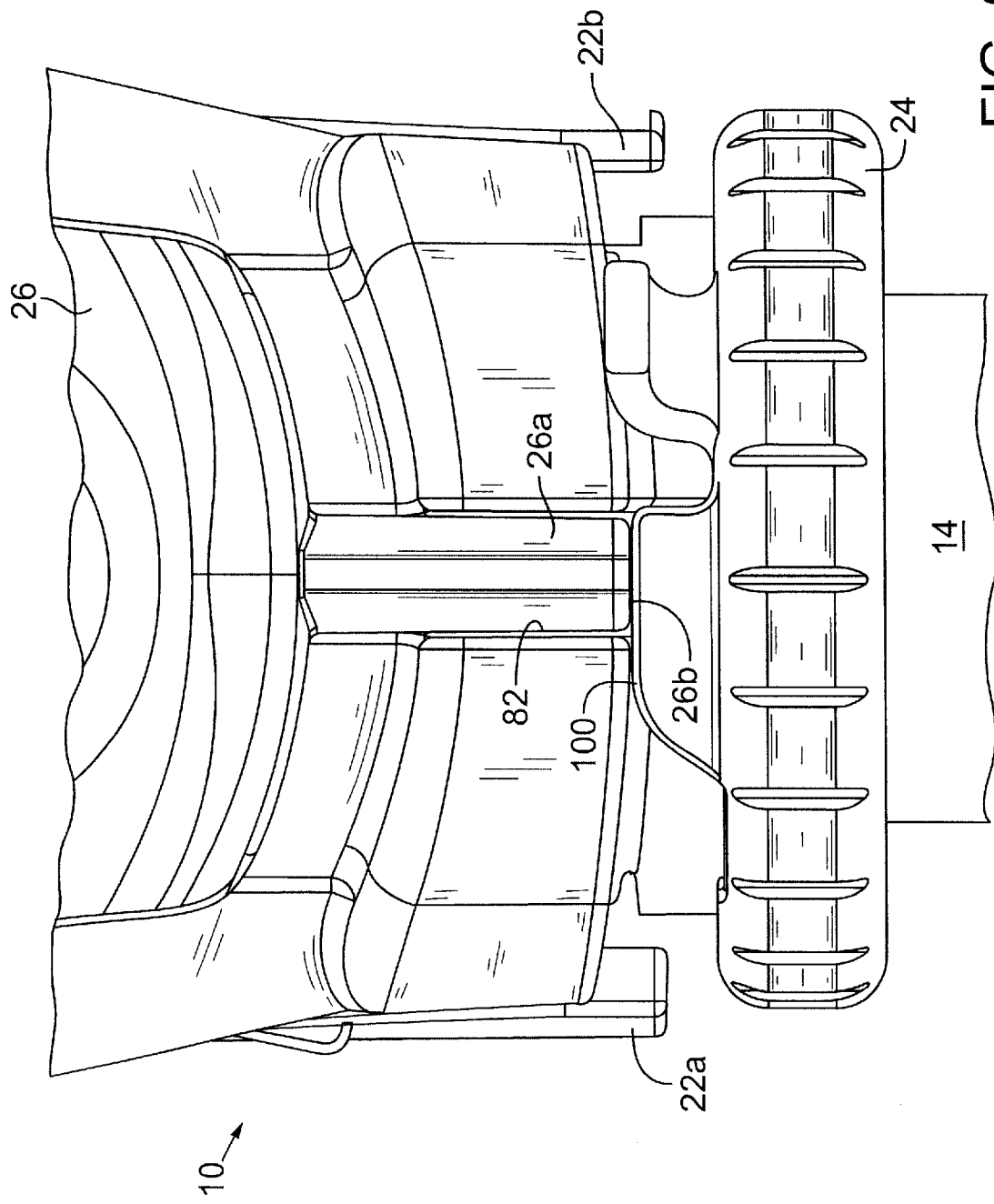

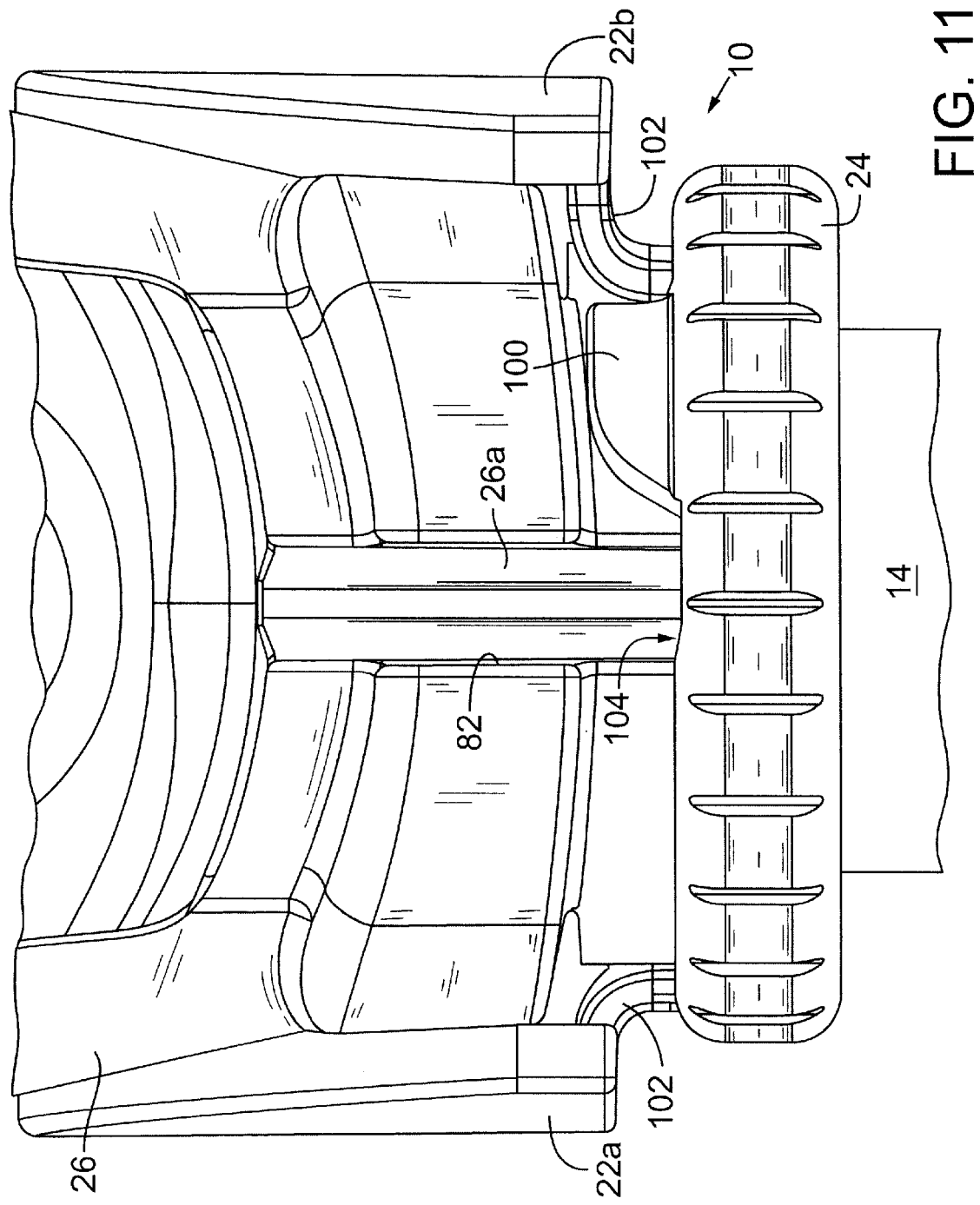

JET INJECTOR APPARATUS AND METHOD

CROSS REFERENCE TO RELATED APPLICATIONS

This application is a Continuation-in-Part of U.S. patent application Ser. No. 09/877,911, entitled "Durable Needleless Jet Injection Apparatus and Method", filed Jun. 8, 2001, and of U.S. patent application Ser. No. 10/057,052, filed Jan. 25, 2002, entitled "Improved Durable Hypodermic Jet Injector Apparatus and Method" the contents of which are incorporated herein by reference to the extent necessary for a complete and enabling disclosure of the present invention.

BACKGROUND OF THE INVENTION

1. Field of the Invention

The present invention relates generally to a durable, multiple-use needle-free (or needle-less) hypodermic jet injection device, and to methods of its making, operation, and use. More particularly, this present invention relates to such a device and to such methods which provide both improved safety and ease of use for a user of the device, as well as providing both improved ease and economy of manufacture and improved durability for the device.

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including:

U.S. Pat. No. 4,596,556, issued Jun. 24, 1986 to J. Thomas Morrow, et al.;

U.S. Pat. No. 4,913,699; issued Apr. 3, 1990 to James S. Parsons; and

U.S. Pat. No. 5,730,723, issued Mar. 24, 1998, to Thomas P. Castellano, et al.

WIPO publication WO 97/37705 also discloses a gas powered disposable needle-less hypodermic jet injector.

Each of these devices has, limitations, deficiencies, or disadvantages, as will be apparent in view of the following detailed description of a single embodiment of the present invention

SUMMARY OF THE INVENTION

In view of the above, it is desirable and is an object for this invention to provide a needle-free jet injection device which reduces the severity of or avoids one or more of the limitations, deficiencies, or disadvantages of the conventional technology.

Particularly, it is an object for this invention to make a needle free injector which is safer to use because by its design, it cannot be activated or discharged to effect an "injection event" while a user of the device is installing or removing an injection cartridge of the device. Safety of use of the device is thus vastly improved.

Further, an object for this invention is to provide such a needle free injector in which certain component parts are so configured, constructed and arranged that they serve at least two functions, and in some cases, plural functions, in the operation and structure of the device.

Thus, it is an object of this invention to provide a durable, needle-free gas-powered hypodermic jet injector including a device body having provision for engaging with and carrying a jet injection cartridge; a gas piston reciprocable in the device body and cooperable with the jet injection cartridge to effect a jet injection in response to communication of pressurized gas to the gas piston; a valve device for effecting communication of pressurized gas to the gas piston in response to movement of the valve device from a first to a second position; and a safety ring rotationally carried on the device body and in a respective first position preventing movement of the valve device from the first to the second position, the safety ring being rotationally movable to a respective second position in which the valve device is movable from the first to the second position.

Further, this present invention provides an improved facility for a user to load and unload a pressurized gas capsule into and from the device.

Accordingly, an embodiment of the present invention provides a device body defining a cavity for receiving therein a pressurized gas capsule, the cavity being closed by a door member pivotally secured to the device body by a hinge pin, and the gas pressure cartridge being impaled at a penetrable diaphragm portion thereof upon a penetrator member of the injection device in response to closing of the door so that gas pressure within the gas pressure cartridge acting on the penetrator member causes a recoil force directed axially of the device; the hinge pin being disposed off axis of the device body so that the recoil force passes off center of the hinge pin in a direction relative to the hinge pin causing a closing torque to be effected on the door.

According to a further aspect this invention provides: a gas powered hypodermic jet injection device including a device body having a forward end; an axially extending recess at the forward end for receiving and retaining an injection cylinder which includes cylinder bore in which an injection piston is sealingly movable to cooperatively define a variable-volume chamber for holding a dose of liquid medication, and a fine-dimension orifice for forming the liquid medication into a high-velocity injection jet in response to forceful movement of the injection piston, the injection cylinder having a pair of diametrically opposite latching lugs projecting radially outwardly at an aft portion thereof; a gas pressure piston sealingly reciprocable in the device body, and forcefully moving the injection piston in the cylinder in response to communication of gas pressure to the gas pressure piston; a valve device for communicating pressurized gas from a source thereof to the gas pressure piston in response to axially forward relative movement of a trigger sleeve outwardly disposed on the device body; a multi-function safety ring rotationally carried on the device body and in a respective first position: a) preventing movement of the valve device from the first to the second position, the safety ring being rotationally movable to a respective second position in which the trigger sleeve of the valve device is movable from the first to the second position, and b) in the first position the safety ring allowing movement of the injection cartridge into and from the recess, in the second rotational position the safety ring both preventing movement into and out of the recess of the injection cartridge; and c) in the first position the safety ring allowing a latching member to move laterally to allow axial insertion of an injection cartridge manually into the recess, and so as to latch with the injection cartridge at the latching lugs thereof, in the second rotational position, the safety ring preventing the latching member from moving laterally so as to prevent unlatching of the latching member from the latching lugs of an injection cartridge disposed in the recess.

Additional objects and advantages of this invention will appear from a reading of the following detailed description of two exemplary preferred embodiments of the invention, taken in conjunction with the appended drawing Figures, in which the same reference numeral is used throughout the several views to indicate the same feature, or features which are analogous in structure or function.

BRIEF DESCRIPTION OF THE DRAWING FIGURES

FIG. 1 provides an exterior perspective view of a durable, needle-free hypodermic jet injector device embodying the present invention;

FIG. 2 is a longitudinal cross sectional view in perspective like FIG. 1;

FIG. 3 provides a longitudinal cross sectional view similar to that of FIG. 2, but is taken at a plane 90 degrees from that of FIGS. 1 and 2;

FIG. 4 is an exploded perspective view of the device seen in FIGS. 1–3;

FIGS. 5 and 6 are each fragmentary cross sectional views similar to respective portions of FIG. 2, and each shows an aft portion of the device, with FIG. 5 showing a loading door opened to receive a pressurized gas cartridge, and FIG. 6 showing the door closed and the pressurized gas cartridge in an operative position preparatory to the effecting of a hypodermic jet injection using the device;

Figure 7:
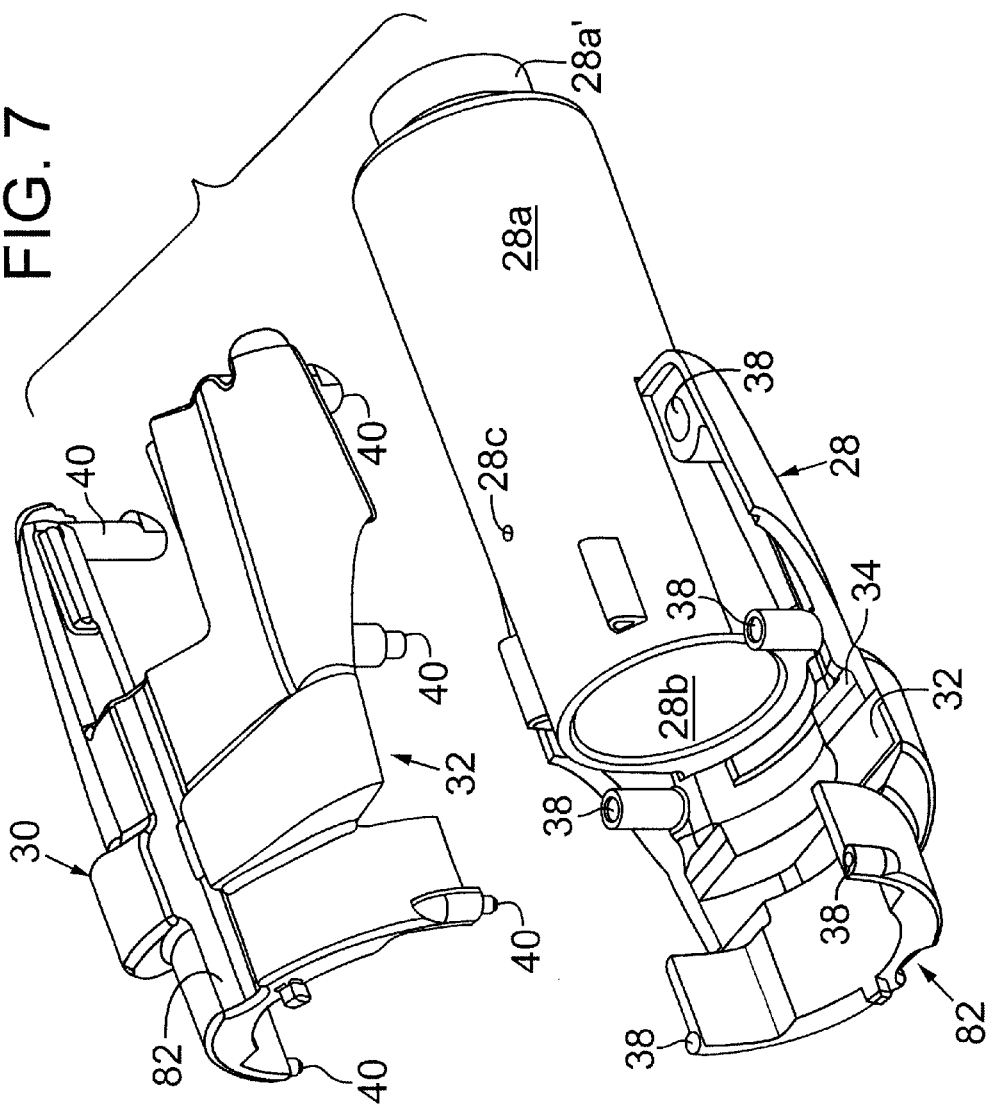
FIG. 7 is a fragmentary exploded perspective view showing component parts of a housing portion of the device.
Figure 13:
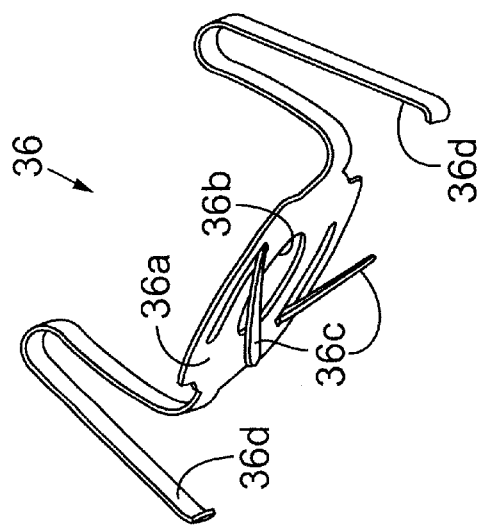
Figure 10B:
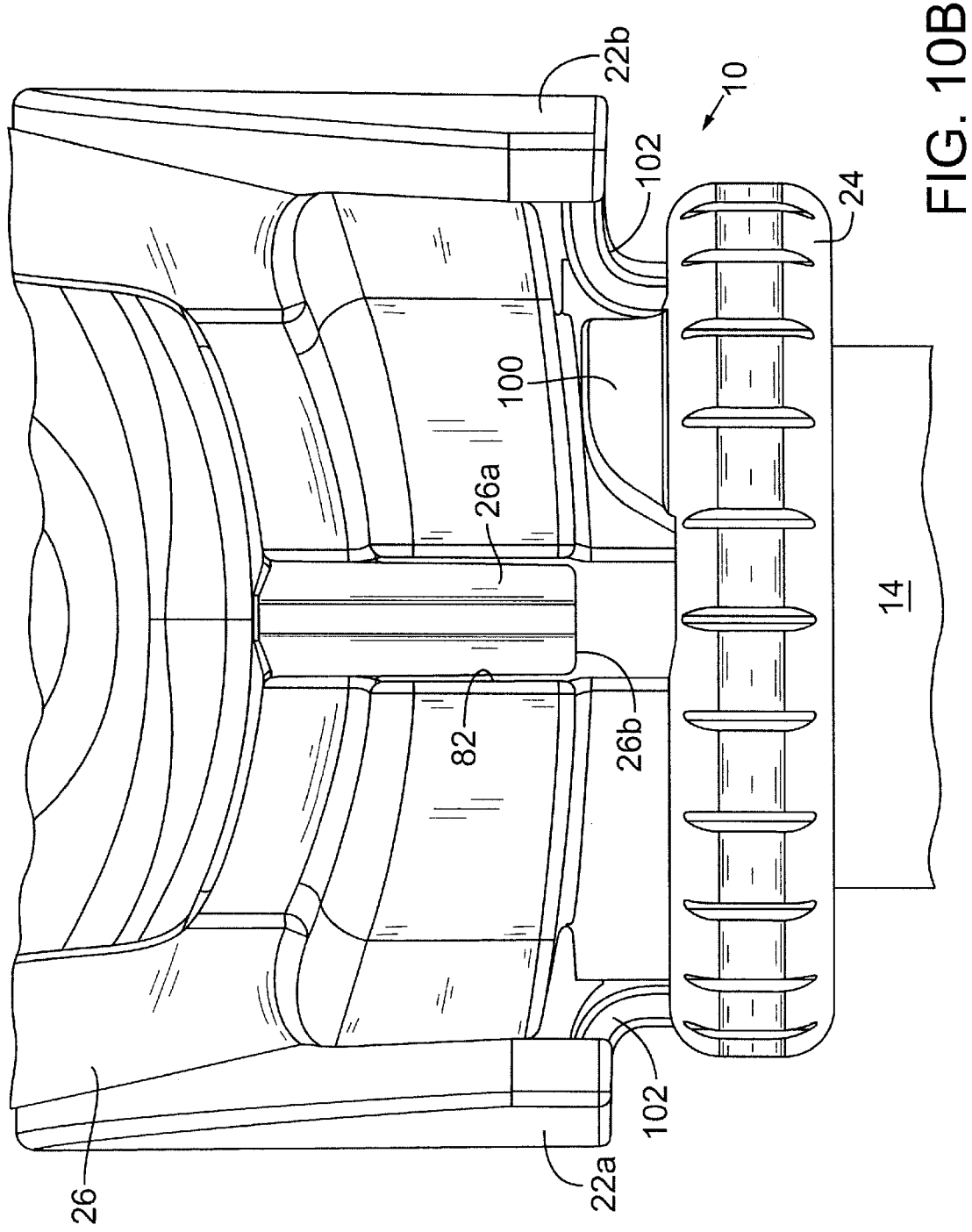
Figure 12:
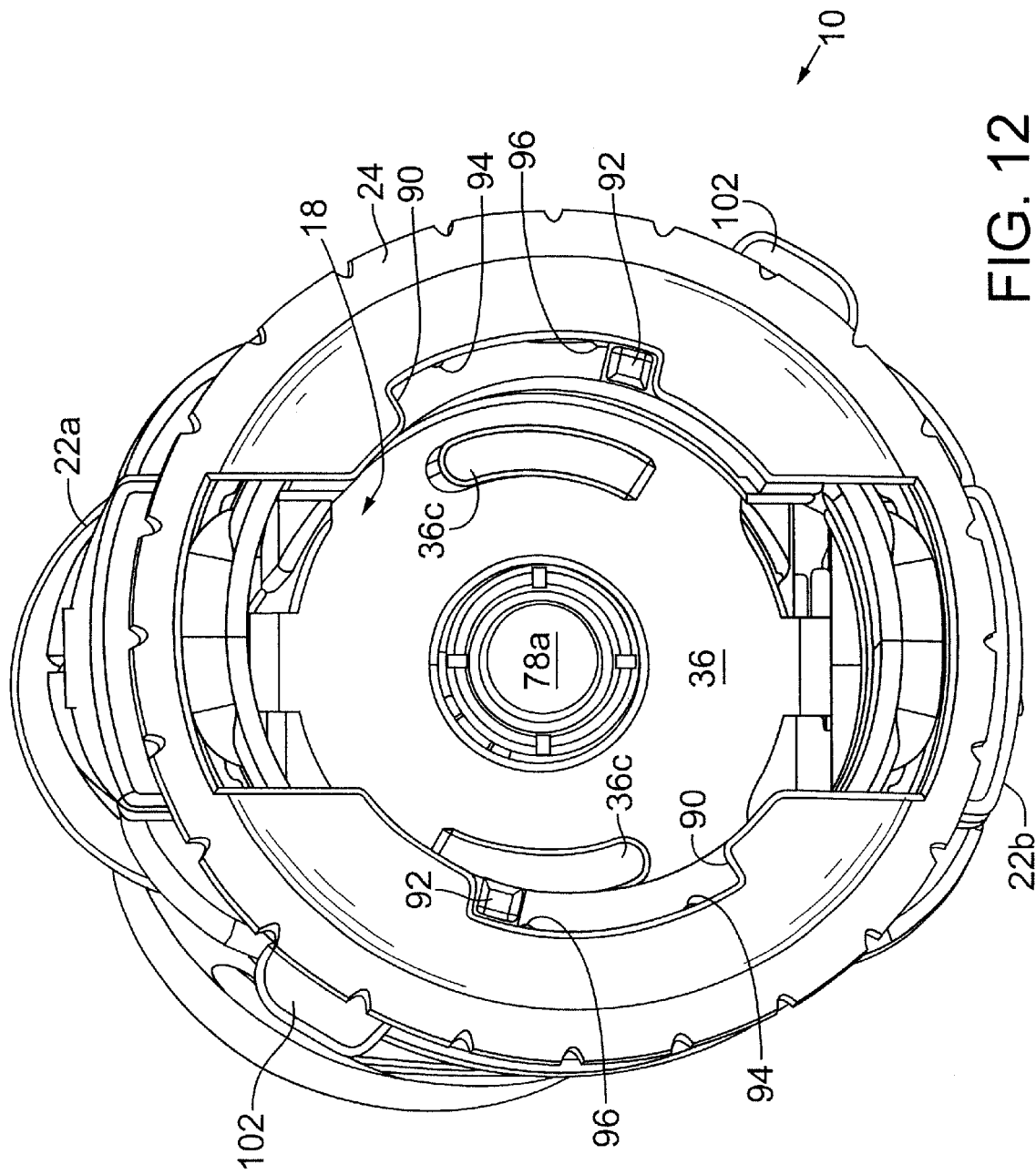
Figure 14:
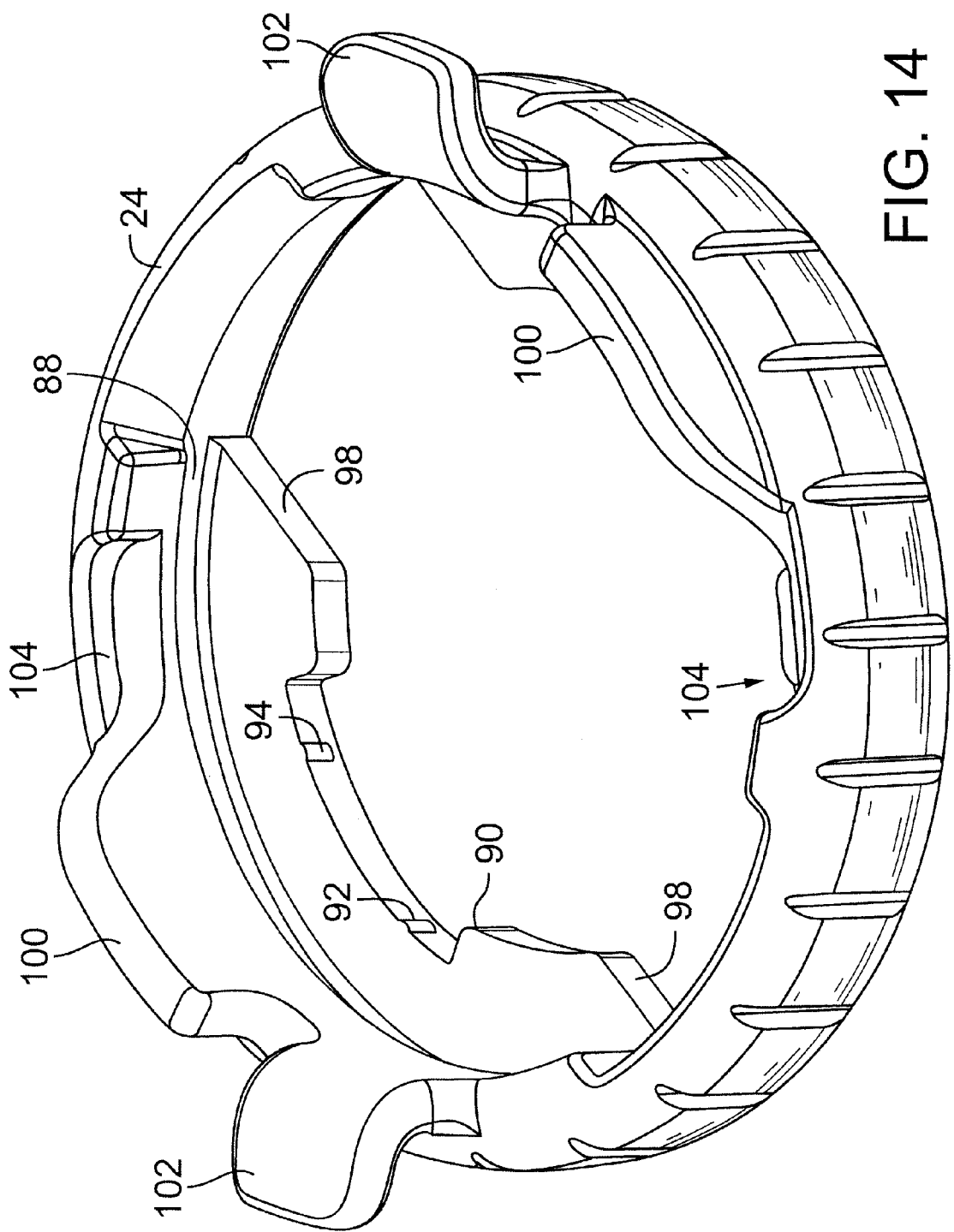
Figure 16:
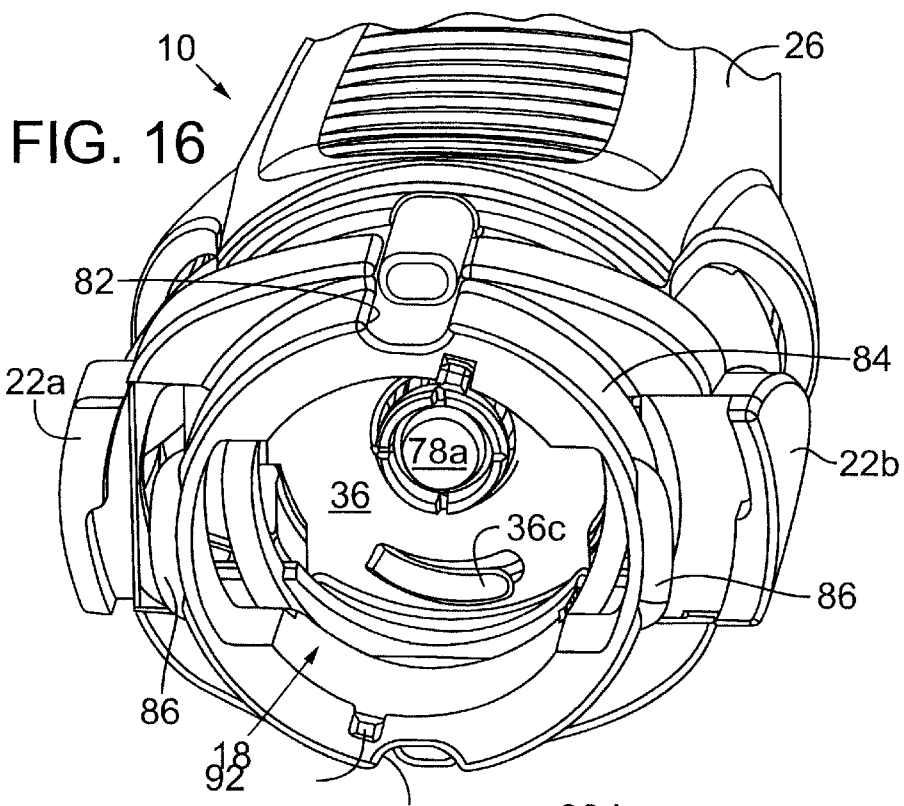
Figure 15:
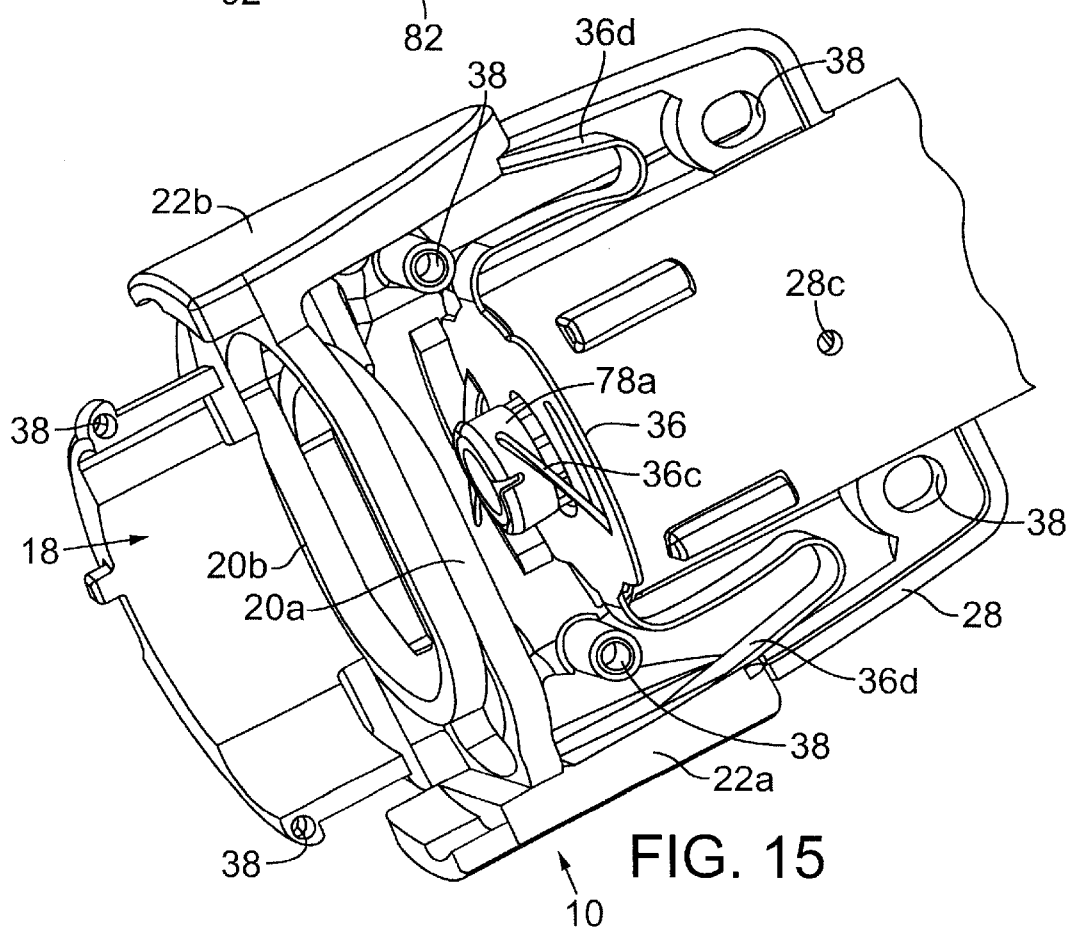

FIG. 8 provides an isolation perspective view of a trigger sleeve portion of the device, which is slidably received over the housing portion seen in FIG. 7;

FIGS. 9a and 9b are related enlarged fragmentary end and side views of the device, each showing a "safety ring" portion of the device in a first relative rotational position allowing for an injection cartridge of the device to be installed or removed, but simultaneously preventing the device from effecting an "injection event";

FIGS. 10a and 10b are related enlarged fragmentary end and side views of the device, each showing the "safety ring" portion of the device in a second relative rotational position preventing both installation and removal of an injection cartridge of the device, and simultaneously allowing the device to effect an "injection event" if the user slides the trigger sleeve forward;

FIG. 11 is a fragmentary side view similar to those seen in FIGS. 9b and 10b, but in FIG. 11 the trigger sleeve has been slid forward, effecting an "injection event" from the device;

FIG. 12 is a fragmentary end view similar to that seen in FIGS. 9a and 10a, but with the injection cartridge removed from the device to illustrate structural details within a recess into which an aft portion the injection cartridge is receivable;

FIG. 13 is an enlarged perspective isolation view of a multi-function spring and guide member which is received between the housing portions seen in FIG. 7, and within the recess of the device seen in FIG. 12;

FIG. 14 is a greatly enlarged perspective isolation view of the "safety ring" of the device, showing structural and functional features defined on the aft side of this safety ring (i.e., on the side or face of the safety ring disposed toward the housing portion of FIG. 7, and not seen in the other drawing Figures);

FIG. 15 is a fragmentary view with some parts removed for clarity of illustration, and shows part of the housing portion of FIG. 7, the multi-function spring and guide member of FIG. 13, a pair of latch members also seen in FIG. 4, and depicts the cooperative relationships of these parts; and FIG. 16 is an enlarged fragmentary perspective view of the forward end of the device with the safety ring removed to for clarity of illustration, and shows retention features of the housing portion for the safety ring.

DETAILED DESCRIPTION OF A EXEMPLARY PREFERRED EMBODIMENT OF THE INVENTION

Overview of the Injection Device

Viewing all of the drawing Figures in conjunction with one another, and particularly viewing first FIGS. 1, 2, 3, and 4, in conjunction, a needle-free, hypodermic jet injection device is illustrated. This device 10 includes a multi-piece housing or "hand piece assembly" 12, which is durable, and reusable. This hand piece assembly 12 removably carries a single-use, disposable injection cylinder assembly 14. The injection cylinder assembly or "injection cartridge" is pre-filled, arranged exclusively for a single-use, and is disposable. The injection cartridge assembly 14 is installed on the device 10 in preparation of a needle free injection, the "injection event" is then effected (i.e., during which a high-velocity jet of liquid medication or other liquid material is delivered into the tissues of a recipient for the injection), and the injection cartridge is removed from the device 10 so that after its use it is properly disposed. Then another "fresh" injection cylinder can be installed on the device for a next subsequent injection.

The injection cartridge 14 has an end surface 14a at which a fine-dimension injection orifice 14b is defined. During an "injection event," as alluded to above, a high velocity jet of liquid medication or other liquid material issues from the orifice 14b, as is indicated by arrow 16 on FIG. 1. This jet 16 has such a high velocity that it is able to penetrate into the skin of a human without the use of a needle. Within the injection cartridge 14 is received a movable outlet valve member 14c (FIG. 3) which in the position shown sealingly closes a flow path leading to the injection orifice 14b. Thus, the injection cartridge 14 contains a pre-measured, sealed dose of medication or other material in preparation for delivering a jet injection. Also received within the injection cartridge 14 is a precision, high strength cartridge cylinder 14d, preferably formed of glass. An injection plunger or piston 14e is reciprocally and sealingly received in the injection cylinder 14d, and in the position seen in FIG. 3 (i.e., for a new injection cartridge 14 which has not yet been used to effect an "injection event") defines a variable-volume chamber 14f. In the chamber 14f is sealingly received (until the moment the outlet valve member 14c is hydraulically forced from its sealing position seen in FIG. 3) the liquid medication or other liquid material that is to be injected by the device 10. As is best seen in FIG. 4, the injection cartridge 14 defines adjacent to an aft end thereof a pair of radially outwardly extending latching lugs 14g (only one of which is visible in FIG. 4—see also FIG. 3). These latching lugs are effective to be respectively engaged by latching surfaces defined on a pair of laterally movable latching plates (to be described further below) in order to securely retain the injection cartridge 14 in a recess 18 at the forward end of the device 10.

Continuing now with an overview of the device 10, it is seen that at a forward end (FIGS. 2, 3, and 12), the hand piece assembly 12 defines axially extending recess 18 into which the aft end portion (i.e., including the latching lugs 14g) of the injection cartridge assembly 14 is received and removably retained. Viewing FIGS. 4 and 15, it is seen that the hand piece assembly 12 slidably carries a pair of apertured latching plates or members 20a and 20b at the recess 18, with each latching plate being resiliently biased (as will be further explained) to a first position in which the latching plates 20a and 20b engage and retain the latching lugs 14g of an injection cartridge assembly 14. These latching members 20a and 20b each include an outwardly disposed "tactile engagement" or finger pad portion 22a and 22b (hereinafter, "finger pads"), which allow the members 20a and 20b to each be slid slightly inwardly and laterally of the hand piece assembly 12 in response to a "pinch" from a user of the device 10 to a second position thus to unlatch from the lugs 14g.

Further, although it is not easily visible in the drawing Figures, the latching lugs 14g of the injection cartridge 14 each define a slight chamfer disposed toward the aft end of the injection cartridge. So, as a result of this chamfer surface, the cartridge 14 may be inserted axially into recess 18 simply by pressing the lugs 14g inwardly past the latching members 22a and 22b, with the chamfer surface wedging the latching members 20a/b momentarily to their second position, after which with further inward motion of the cartridge into recess 18, these latching members "snap back" to engage the lugs 14g. Once the latching members 20a/b have snapped back to their first position, then they securely retain the injection cartridge 14 within recess 18 at the forward end of hand piece assembly 12.

Also at the forward end of the handpiece assembly 12, surrounding the recess 18 and providing controlled access to (and also controlling egress of cartridge 14 from) this recess 18, is a "safety ring" 24 which is rotationally carried on the hand piece assembly 12. The safety ring 24 is rotationally movable through a relatively limited angle of movement between two detented (i.e., tactile, or "touch sensible") operative positions, as will be further explained. The safety ring 24 in a first (FIGS. 9a, 9b, and 12) position allows the injection cartridge 14 to be installed into or removed from the recess 18 on the handpiece assembly 12 (i.e., with removal requiring manual operation of the latch plates 20a and 20b via finger pads 22a/b). However, in this first position the safety ring 24 also blocks or prevents forward relative motion from a first axial position to a second axial position of a trigger sleeve portion 26 of the handpiece assembly 12. The trigger sleeve 26, by being retained in a rearward or first position, and by being prevented from forward relative motion to its second position also prevents the device 10 from effecting an injection event while the safety ring is in its first rotational position.

On the other hand, the safety ring 24 is rotationally movable manually from the first detented position to a second detented position (FIGS. 10a, 10b), and in this second position of the safety ring, the trigger sleeve 26 is not blocked in its first axial position, and is allowed to slidably move relatively forward to a second axial position (as will be explained in greater detail below—see FIG. 11). If in preparation to movement of the trigger sleeve 26 to its second position, the device has been properly prepared by it's user for effecting a jet injection (as will be further explained, but this requires the installation of a new injection cartridge 14 and of a new pressurized gas cartridge—to be further identified below), then forward movement of the trigger sleeve 26 to its second position will cause the device to effect an injection event (recalling arrowed numeral 16 of FIG. 1).

Having considered the highlights of the device 10, attention may now be directed to FIG. 4 for an overview of the component parts of the device. Parts 14–26 have already been introduced. But, viewing FIG. 4 with some attention to detail will reveal that the handpiece assembly 12 includes a first housing portion 28 (best seen also in FIG. 7) which integrally forms or defines a cylinder part 28a defining a stepped through bore 28b. This bore has a threaded smaller diameter portion 28b' (FIGS. 2, 3, and 5) which opens toward the aft end of the housing 12 within a reduced diameter axially extending bore portion 28a' of the housing 12. A vent hole 28c opens outwardly from the bore 28b on the housing portion 28. The location of vent hole 28c is selected to be intermediate of the ends of bore 28b. A second housing portion 30 mates with the first housing portion 28 to cooperatively form the recess 18, and to provide both a pair of laterally extending guide ways 32 (FIG. 7), and to provide a recess 34 for receiving and retaining a multi-function spring and guide member 36 (best seen in FIG. 13, but see also FIG. 15).

Considering for a moment this multi-function spring and guide member 36, as it is best seen in FIG. 13, it is seen that this member includes a central plate-like portion 36a, which defines a central guide hole 36b. Axially from the central plate like portion 36a extends a diametrically opposite pair of arcuate axial spring fingers or portions, 36c. As will be seen, these spring fingers 36c engage the aft end of the injection cartridge 14 in recess 18, to bias or urge this injection cartridge (once used), out of the recess 18 when the user depresses the finger pads 22a/b. Also defined by the multi-function spring and guide member 36 is a diametrically opposite pair of axially and radially extending radial spring arms 36d. These spring arms individually engage a respective one of the latch members 20a/b (as is seen best in FIG. 15) in order to urge the latch member 20a/b laterally outwardly of the housing 12, and into a first position in which they are engageable with the latching lugs 14g. The plate-like portion 36a and central guide hole 36b have additional functions to be further described below.

Returning to FIG. 7, it is seen that the first housing portion 28 defines an array of laterally extending guide bores or recesses, each referenced with the numeral 38. Similarly, on housing portion 30 is defined a matching array of laterally extending pins or latching protrusions, each referenced with the numeral 40. When the housing portions 28 and 30 are united, the pins or latching protrusions 38 enter the guide bores or recesses 40 and mutually cooperate in retaining the housing portions 28 and 30 together.

Returning again to a consideration of FIG. 4, it is seen that in assembling the device 10, a valve rod 42 having a threaded portion 42a, and a head portion 42b, is first inserted into the bore 28b, and is threaded into permanent sealing engagement with the housing 12. Upon the protruding portion of this valve rod 42 (FIGS. 2, 3, 5, and 6) is received a trigger return spring 44, followed in sequence by the trigger sleeve 26 (which is received slidably over the housing portions 28 and 30), an O-ring seal member 46, a ring-like trigger insert 48, another O-ring seal member 50, a trigger washer 52, a housing back portion 54 (which seats on an axial shoulder at a reduced diameter threaded portion 42c of the valve rod 42, and a retaining nut 56. The retaining nut is tightened on the portion 42a in order to retain the back housing portion, and to captively and movably retain the trigger sleeve member 26, and its associated valving parts (i.e., the O-ring seal members 46, 50, trigger insert 48, and trigger washer 52). The trigger return spring 44 biases the trigger sleeve 26 to a first position toward the aft end of the housing 12, and this trigger sleeve 26 is manually movable to a first position (provided that safety ring 24 is rotated to its second position) so that an injection event is effected by the device 10. The valve rod 42 carries a penetrator member 58 which is axially disposed and presented within a cavity 54a of the housing back portion 54 (FIGS. 2, 3, 5, and 6).

Pivotally carried at and in one position closing the cavity 54a is a door member 60 having a wing portion 60a which in the closed position of the door member 60 overlies the cavity 54a and closes this cavity. The door member 60 includes a boss portion 60b received pivotally between a pair of ears 54b of the back housing portion, and which define aligned bores 54c. The boss portion 60b defines a through bore 60c aligning with the bores 54c. A pin 62 is received retainingly in the bore 60c, and has end portions that are pivotal in the ears 54b (i.e., at bores 54c) so that the pin 62 provides a hinge for the door member 60.

Viewing FIGS. 5 and 6, it is seen that the pin 62 is disposed off axis with respect to an axial line 64 extending aft from the center of the penetrator member 58. The significance of this off center position of the pin 62 can best be appreciated by a consideration of FIGS. 5 and 6. In FIG. 5, the door 60 is shown opened for receipt into the cavity 54a of a pressurized gas cartridge 66. The cartridge 66 at a forward end has a penetrable diaphragm portion 66a, as will be well understood by those ordinarily skilled in the pertinent arts. The door 60 provides engagement surfaces and a camming action that will force the aft end of the cartridge 66 into the cavity 54a, so as to sealingly impale the diaphragm 66a of the cartridge 66 on the penetrator member 58. The result of closing the door 60 with a cartridge 66 positioned as seen in FIG. 5 is seen best in FIG. 6, with the door 60 in its closed position, and with a pressurized gas cartridge 66 disposed in the cavity 54a and penetrated at penetrable diaphragm portion 66a upon the penetrator member 58. Because of the pressurized gas that is captured (i.e., captured up until the moment this gas pressure is utilized to effect an injection event) in the gas cartridge 66, this cartridge attempts to recoil off of the penetrator member. That is, a recoil force about equal to the gas pressure level within the cartridge 66 times the area of the penetrator member 58 is effective on the cartridge 66. Although the area of the penetrator member 58 is small, the gas pressure in the cartridge 66 may be well over 1000 psi (pounds per square inch), and may be several thousand psi. Thus, the recoil force effective on the gas cartridge 66 is not insignificant. This recoil force (represented by arrow 68 in FIG. 6) is effective along an axial line, which is seen to pass off center of the hinge pin 62. Thus, because of this force 68 a closing torque on door 60 is effective to assist in keeping this door closed so long as the cartridge 66 has high pressure gas in it (i.e., prior to an injection event). As is also seen in FIG. 6, the forward edge of door wing 60a defines a protruding latch ridge 70, which is received into a latch recess 72 when the door member 60 is in its closed position. The latch ridge 70 and latch recess 72 are effective to retain the door member 60 in its closed position even when there is no gas cartridge in the recess 54a. It will be understood that because after an injection event the gas pressure in cartridge 66 drops to essentially ambient, the closing torque on door 60 disappears, and the door 60 is then easily opened manually. Users of the device 10 will quickly learn when memory fails to judge whether a pressurized or used cartridge is in cavity 54a by the resistance (or absence of resistance) to opening of the door 60.

Returning again to FIG. 4 (and to FIGS. 2 and 3), it is seen that received into the bore 28b is a gas piston 74 carrying an O-ring seal member 76. The gas piston sealingly and movably cooperates with the cylinder portion 28a of first housing portion 28. The gas piston 74 defines a gas piston stem 78, with a forward end portion 78a, which extends forwardly and is receivable into the aft end of the injection cartridge 14 in order to abut and move injection piston 14e forcefully forward during an injection event (i.e., causing injection jet 16, recalling FIG. 1). Received over and carried upon the gas piston stem portion 78 is a return spring 80. Viewing FIG. 4 (and FIGS. 2 and 3), it is seen that this return spring 80 at its forward end seats against the aft surface of the central plate portion 36a of the multi-function spring and guide member 36. That is, this member 36 serves four functions, of guiding the forward end of the gas piston stem s so that this stem is generally centered in the bore 28a even in the absence of an injection cartridge 14 in the recess 18, of providing a seat for the forward end of spring 80, and of providing integral spring portions 36c effective to urge the injection cartridge 14 out of recess 18, and integral portions 36d to urge the latch members 20a/b to their first positions latching the injection cartridge 14 within recess 18.

Returning to a consideration of FIG. 8, it is seen that the trigger sleeve 26 includes a pair of diametrically opposite and axially forwardly extending projections 26a, which respectively define a pair of end surfaces 26b. On the housing portions 28 and 30 are a pair of diametrically opposite and axially extending grooves, each indicated with the numeral 82, and best seen in FIGS. 7, 9b, 10b, 11, and 16. The projections 26a of the trigger sleeve 26 are received movably in the grooves 82, and project along these grooves 82 forwardly toward the safety ring 24. As is seen in FIGS. 9b, 10b, and 11, the end surfaces 26b of the projections 26a may engage particular features of the safety ring 24 in order to either prevent forward movement of the trigger sleeve 26 from its first position to a second position, or to perform yet another function (to be described below) upon forward movement for this trigger sleeve to its second position.

As is seen in FIG. 16, the housing 12 also defines a bearing surface 84, upon which the safety ring 24 is rotationally received. A pair of diametrically opposite radially outwardly extending ribs 86 are defined at a forward margin of the bearing surface 84, and serve to captively retain the safety ring on bearing surface 84 by being received captively and movably into a circumferential groove 88 (viewing FIG. 14) of this safety ring 24. In other words, once the safety ring 24 is forced axially onto the bearing surface and axially past these ribs 86, it is not easily removed from the housing 12. In order to limit the rotational freedom of the safety ring 24, a central plate like portion 24a of this ring defines a pair of diametrically opposite arcuate recesses 90 (only one of which is visible in FIG. 14, but see FIGS. 9a, 10a, and 12). The housing 12 defines a diametrically opposite pair of axial pin like protrusions 92. These protrusions are received into the arcuate recesses 90, and engage the opposite ends of these recesses to define two limits (i.e., respective first and second rotational positions) for the safety ring 24 on the housing 12. Further, the arcuate recesses each have a pair of circumferentially spaced apart radially inwardly extending detent bumps 94 and 96, each disposed adjacent to a respective end of the arcuate recesses 90. The bumps 94 and 96 are of fine-dimension, and are of sufficiently low radial height that the pins 92 can be moved circumferentially past these bumps, but also are of sufficient radial height that as the ring 24 is manually moved rotationally relative to the housing 12, the bumps 94, 96 can be felt as tactile detent features in the rotational position of the safety ring 24. Thus, the safety ring 24 is provided with two detented limit positions, one adjacent to each extreme of its rotational movement relative to housing 12.

The central plate-like portion 24a of safety ring 24 also defines a pair of diametrically opposite radially extending "windows" 98, which provide for the latching lugs 14g of the injection cartridge to pass through these windows only when the safety ring is in its first relative rotational position (i.e., in a "safe" position). Conversely, when the safety ring is not in its first relative rotational position, and when it is in its second rotational position (i.e., the "activate" position), the plate like portion 24a interferes with the latching lugs to prevent the injection cartridge from moving axially either in or out of the recess 18. Thus, a user cannot install a cartridge 14 into recess 18 unless that safety ring 24 is first placed in its first position, making the device 10 "safe."

Further considering the safety ring as seen in FIG. 14, and in FIGS. 9a and 9b, it is seen that the safety ring 24 includes a pair of axially extending cam surfaces confronting the end surfaces 26b of the projections 26a of trigger sleeve 26 in the first (i.e., "safe") position of the safety ring 24. Thus, when the safety ring 24 is in this first or "safe" rotational position as seen in FIGS. 9a and 9b, the trigger sleeve is positively prevented from moving forward from its first to its second position. In this "safe" position of the safety ring 24, the user may install a new injection cartridge 14 into recess 14, or remove a used injection cartridge 14 from recess 18 by depressing the latch members 20a/b by applying a pinch to the finger pads 22a/b. When the latch members 20a/b unlatch from the latching lugs 14g, the used cartridge 14 is at least partially ejected from recess 18 by the axial spring fingers 36c.

Conversely, when the safety ring 24 is manually rotated to its second or "activate" rotational position (recalling that this safety ring "detents" in each of the "safe" and "activate" positions so that these positions of the safety ring can be sensed by tactile contact with the safety ring 24 of the device 10, the cam surfaces 100 are moved out of alignment with the projections 26a. In this "activate" position of the safety ring 24, a pair of radially outwardly extending diametrically opposite protrusion 102 each individually engage under a respective one of the pair of finger pads 22a/b so as to prevent the latching plates being moved inadvertently to their second position. This is a primary safety feature, preventing accidental release of the injection cartridge 14 from within recess 18. Thus, during an injection event, the cartridge 14 cannot be accidentally released from its engagement with the device 10 via the latch plates 20a/b. As noted above, a secondary and backup safety feature is provided by the location of the "windows" 98 of the plate like portion of safety ring 24. Because these windows 98 are out of alignment with the latching lugs when the safety ring 24 is in its second or "activate" position, the injection cartridge is also retained in this way in the recess 18. That is, it is recalled that the safety ring 24 itself has a plate like portion 24a which in its second (or "activate") relative rotational position prevents the injection cartridge 14 from moving either in or out of the recess 18. Thus, during an injection event, a redundant retention of the injection cartridge 14 within recess 18 is effected.

Now viewing FIG. 11 in conjunction with FIG. 14, it is seen that when a user of the device 10 slides the trigger sleeve 26 forward to its second position to effect an injection event, the forward portion of the projections 26a actually extend into respective ones of a pair of diametrically opposite axial and radial recesses 104 of the safety ring 24. Thus, after the injection event, in the event that the trigger sleeve 26 does not return to its first position, the safety ring is blocked from being turned from its second position back to its first position. This condition of the device 10 provides an incentive for the user of the device to manually insure that the trigger sleeve 26 is returned fully to its first position, in preparation for installation of a new gas cartridge into the device. Once the trigger sleeve is fully returned to its first position, then the safety ring 24 is free to be manually turned from its second (i.e., "activate") position, back to its first (i.e., "safe") position, allowing the used injection cartridge to be removed from the device 10, and so that this used cartridge may be properly disposed of. A new injection cartridge then may also be engaged onto the device with the safety ring 24 in its "safe" position. Preferably, this loading of a new injection cartridge 14 onto the device 10 is performed before a new gas cartridge 66 is loaded into the device. The safety ring 24, by its engagement with the trigger sleeve 26 after an injection event helps assure that this preferred sequence of reloading events is observed by users of the device. However, even in the event that a user of the device first loads a new gas cartridge 66, and then loads a new injection cartridge 14, the safety features of this device by their interaction and cooperation insure that the user is safe during reloading of the device, and that the device does not effect an injection event until the user is ready and takes deliberate action to cause this injection event.

While the invention has been depicted and described by reference to a particularly preferred embodiment of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

We claim:

1. A gas powered hypodermic jet injection device, said device comprising:

a device body having provision for engaging with and carrying a jet injection cartridge;

a gas piston reciprocable in said device body and cooperable with the jet injection cartridge to effect a jet injection in response to communication of pressurized gas to said gas piston;

a valve device for effecting communication of pressurized gas to said gas piston in response to movement of said valve device from a first to a second position;

a safety ring rotationally carried on said device body and in a respective first position preventing movement of said valve device from said first to said second position, said safety ring being rotationally movable to a respective second position in which said valve device is movable from said first to said second position; and at least two tactile detents disposed on said device body such that each of said tactile detents provides a detented limit position corresponding to either said first position or said second position of said safety ring.

2. A gas powered hypodermic jet injection device, said device comprising:

a device body having provision for engaging with and carrying a jet injection cartridge, wherein said device body further includes a latching member in a respective first position securing the jet injection cartridge to said device body, and in a respective second position said latch member allowing said jet injection cartridge to engage with or disengage from said device body;

a gas piston reciprocable in said device body and cooperable with the jet injection cartridge to effect a jet injection in response to communication of pressurized gas to said gas piston;

a valve device for effecting communication of pressurized gas to said gas piston in response to movement of said valve device from a first to a second position; and a safety ring rotationally carried on said device body and in a respective first position preventing movement of said valve device from said first to said second position, said safety ring being rotationally movable to a respective second position in which said valve device is movable from said first to said second position, said safety ring including a portion which in said respective second position of said safety ring aligns with and blocks said latch member from moving from said first position of said latch member to said second position of said latch member.

3. The jet injection device of claim 2 wherein in said respective first position of said safety ring, said portion of said safety ring is moved out of alignment with said latch member, so that in said second position of said safety ring said latch member is movable to said second position of said latch member.

4. The jet injection device of claim 2 wherein said device defines a recess extending axially and including a pair of lateral extensions for receiving latching lugs carried on said injection cartridge, said safety ring including a plate-like portion partially closing a forward side of said safety ring, and defining an aperture matching said recess in shape to receive said injection cartridge including said latching lugs, in said first position of said safety ring, said aperture of said safety ring being congruent with said recess to allow said injection cartridge to move axially in and out of said recess; and in said second position of said safety ring, said aperture being rotationally disposed relative to and non-congruent with said recess so that said injection cartridge is either trapped in said recess or prevented from entering said recess by confrontation of said latching lugs with respective portions of said plate-like portion of said safety ring.

5. The jet injection device of claim 2 wherein said latching member includes a latch plate slidably movable laterally of said device body, and said latch plate defining an aperture through which a portion of said injection cartridge is received, said device including a plate-like spring member including an axially and radially extending spring arm portion, and said spring arm portion yieldably engaging said latch plate to yieldably bias said latch plate to a first position in which it latchingly engages said injection cartridge, said latch plate including an outwardly disposed finger pad by which said latch plate may be moved to a second position unlatching from said injection cartridge, and said axially and radially extending spring arm of said plate-like spring member elastically yielding to allow movement of said latch plate member to said second position.

6. The jet injection device of claim 2 wherein said latching member includes a latch plate slidably movable laterally of said device body, and said latch plate defining an aperture through which a portion of said injection cartridge is received, said device including a plate-like spring member including an axially and radially extending spring arm portion, and said spring arm portion yieldably engaging said latch plate to yieldably bias said latch plate to a first position in which it latchingly engages said injection cartridge, said latch plate including an outwardly disposed finger pad by which said latch plate may be moved to a second position unlatching from said injection cartridge, and said axially and radially extending spring arm of said plate-like spring member elastically yielding to allow movement of said latch plate member to said second position.

7. The jet injection device of claim 6 wherein said plate-like spring member further includes an axially and circumferentially extending spring finger confronting a portion of said injection cartridge, said device body including a recess into which said injection cartridge is receivable to be engaged by and carried by said device body, said recess leading to said plate-like spring member, so that said spring finger is engaged by said injection cartridge and urges said injection cartridge out of said recess.

8. The jet injection device of claim 6 wherein said gas piston further includes an axially extending stem, said plate-like spring member defining a centrally disposed guide hole, an a forward portion of said gas piston stem extending through and being guided in reciprocation by said guide hole in alignment with said injection cartridge.

9. The jet injection device of claim 6 wherein said device further includes a return spring at one end bearing upon said gas piston and urging said gas piston to a first position in preparation for receiving pressurized gas communicated thereto, said plate-like spring member opposing said return spring at an opposite end so that opposite end of said return spring seats upon said plate-like spring member.

10. A gas powered hypodermic jet injection device, said device comprising:

a device body having provision for engaging with and carrying a jet injection cartridge;

a gas piston reciprocable in said device body and cooperable with the jet injection cartridge to effect a jet injection in response to communication of pressurized gas to said gas piston;

a valve device for effecting communication of pressurized gas to said gas piston in response to movement of said valve device from a first to a second position;

a safety ring rotationally carried on said device body and in a respective first position preventing movement of said valve device from said first to said second position, said safety ring being rotationally movable to a respective second position in which said valve device is movable from said first to said second position;

said valve device including a projection extending toward said safety ring, and said projection moving between a respective first disposition and a second disposition in response to movement of said valve device between said first position of said valve device and said second position of said valve device;

said safety ring including a cam surface which in said first position of said safety ring confronts and is engageable by said projection, thus to prevent said valve device from moving from said first position of said valve device to said second position of said valve device.

11. The jet injection device of claim 10 wherein said safety ring further includes an axial and radially extending recess which in said second position of said safety ring aligns with and into which said projection of said valve device is receivable upon movement of said valve device from said first position of said valve device to said second position of said valve device.

12. The jet injection device of claim 11 wherein said projection of said valve device when received into said axially and radially extending recess of said safety ring in said second position of said valve device prevents rotational movement of said safety ring from said second position of said safety ring to said first position of said safety ring.

13. A gas powered hypodermic jet injection device, said device comprising:

a device body having provision for engaging with and carrying a jet injection cartridge;

a gas piston reciprocable in said device body and cooperable with the jet injection cartridge to effect a jet injection in response to communication of pressurized gas to said gas piston;

a valve device for effecting communication of pressurized gas to said gas piston in response to movement of said valve device from a first to a second position;

a safety ring rotationally carried on said device body and in a respective first position preventing movement of said valve device from said first to said second position, said safety ring being rotationally movable to a respective second position in which said valve device is movable from said first to said second position; and wherein said device body defines a cavity for receiving a gas pressure cartridge, said device body further including a door hingably attaching to said device body by means of a hinge pin, and said gas pressure cartridge being impaled at a penetrable, diaphragm portion thereof upon a penetrator member of said injection device in response to closing of said door so that gas pressure within said gas pressure cartridge acting on said penetrator member causes a recoil force directed axially of said device; said hinge pin being disposed off axis of said device body so that said recoil force passes off center of said hinge pin in a direction relative to said hinge pin causing a closing torque to be effected on said door.

14. A gas powered hypodermic jet injection device, said device comprising:

a device body having a forward end; an axially extending recess at said forward end for receiving and retaining an injection cylinder which includes cylinder bore in which an injection piston is sealingly movable to cooperatively define a variable-volume chamber for holding a dose of liquid medication, and a fine-dimension orifice for forming the liquid medication into a high-velocity injection jet in response to forceful movement of the injection piston, the injection cylinder having a pair of diametrically opposite latching lugs projecting radially outwardly at an aft portion thereof;

a gas pressure piston sealingly reciprocable in said device body, and forcefully moving said injection piston in said cylinder in response to communication of gas pressure to said gas pressure piston a valve device for communicating pressurized gas from a source thereof to said gas pressure piston in response to axially forward relative movement of a trigger sleeve outwardly disposed on said device body;

a multi-function safety ring rotationally carried on said device body and in a respective first position;
 a) preventing movement of said valve device from said first to said second position, said safety ring being rotationally movable to a respective second position in which said trigger sleeve of said valve device is movable from said first to said second position, and
 b) in said first position said safety ring allowing movement of said injection cartridge into and from said recess, in said second rotational position said safety ring both preventing movement into and out of said recess of said injection cartridge; and
 c) in said first position said safety ring allowing a latching member to move laterally to allow axial insertion of an injection cartridge manually into said recess, and so as to latch with said injection cartridge at the latching lugs thereof, in said second rotational position, said safety ring preventing said latching member from moving laterally so as to prevent unlatching of said latching member from the latching lugs of an injection cartridge disposed in said recess.

15. The jet injection device of claim 14 wherein said latching member of said device includes a pair of plate-like latching parts, each latching part defining a respective aperture receiving therethrough an aft portion of the injection cartridge including the latching lugs, each of said plate-like latching parts respectively engaging one of the latching lugs of the injection cylinder, and each latching part including a respective oppositely-disposed finger pad outwardly disposed on said device, said safety ring in said second rotational position including a pair of portions each blocking lateral movement of a respective one of said pair of said latching parts of said latching member by engaging beneath a respective one of said finger pads and preventing the respective latching part from disengaging from the latching lugs of the injection cartridge.

16. The jet injection device of claim 15 wherein in said respective first position of said safety ring, said portions of said safety ring is moved out of alignment with said finger pads of said pair of latching parts, so that in said first position of said safety ring said latch member is movable to said second position of said latch member and said injection cartridge is movable into and out of said recess.

17. The jet injection device of claim 14 in which said trigger sleeve of said valve device include a diametrically opposite pair of projections each extending axially along a respective exterior surface of said device and toward said safety ring, and in response to movement of said trigger sleeve between said first and said second positions for said valve device said pair of projections moving axially between a respective first place respectively spaced from said safety ring and respectively in engagement with said safety ring;

said safety ring including a diametrically opposite pair of cam surfaces which in said first position of said safety ring confronts and is engageable by said projections, thus to prevent said trigger sleeve of said valve device from moving from said first position of said valve device to said second position of said valve device.

18. The jet injection device of claim 17 wherein said safety ring further includes a diametrically opposite pair of axially and radially extending recesses which in said second position of said safety ring each aligns with and into which a respective one of said pair of projections of said trigger sleeve of said valve device is receivable upon movement of said valve device from said first position of said valve device to said second position of said valve device.

19. The jet injection device of claim 18 wherein said pair of projections of said trigger sleeve of said valve device when received into said axial and radially extending recesses of said safety ring in said second position of said safety ring and of said valve device cooperatively prevent rotational movement of said safety ring from said second position of said safety ring to said first position of said safety ring.

20. The jet injection device of claim 14 wherein said device defines a recess extending axially and including a pair of lateral extensions for receiving the diametrically opposite pair of latching lugs of the injection cartridge, said safety ring including a plate-like portion partially closing a forward side of said safety ring, and said plate-like portion of said safety ring further defining an especially contoured aperture matching said recess in shape to in said first rotational position of said safety ring receive through said aperture an aft portion of said injection cartridge including said latching lugs, so that in said first position of said safety ring said aperture being congruent with said recess to allow said injection cartridge to move axially in and out of said recess; and in said second position of said safety ring said aperture being rotationally disposed relative to and non-congruent with said recess so that said injection cartridge is either trapped in said recess by confrontation of the latching lugs with said plate-like portion of said safety ring, or is prevented from entering said recess also by confrontation of said latching lugs with respective portions of said plate-like portion of said safety ring which at least partially overlie said pair of lateral extensions of said recess.

21. A jet injection device including a device body defining a cavity for receiving therein a pressurized gas capsule, said cavity being closed by a door member pivotally secured to said device body by a hinge pin, and said gas pressure cartridge being impaled at a penetrable diaphragm portion thereof upon a penetrator member of said injection device in response to closing of said door so that gas pressure within said gas pressure cartridge acting on said penetrator member causes a recoil force directed axially of said device; said hinge pin being disposed off axis of said device body so that said recoil force passes off center of said hinge pin in a direction relative to said hinge pin causing a closing torque to be effected on said door.

22. A gas powered hypodermic jet injection device, said device comprising:
  a device body having a forward end; an axially extending recess at said forward end for receiving and retaining an injection cylinder which includes cylinder bore in which an injection piston is sealingly movable to cooperatively define a variable-volume chamber for holding a dose of liquid medication, and a fine-dimension orifice for forming the liquid medication into a high-velocity injection jet in response to forceful movement of the injection piston, the injection cylinder having a pair of diametrically opposite latching lugs projecting radially outwardly at an aft portion thereof;
  a gas pressure piston sealingly reciprocable in said device body, and including an axially forwardly extending stem portion engaging with and forcefully moving said injection piston in said cylinder in response to communication of gas pressure to said gas pressure piston;
  a pair of latching plate members each laterally movable of said device body and each respectively engaging in a first position with one of said pair of latching lugs of said injection cartridge, in a second position said latching plate members disengaging from said latching lugs to allow said injection cartridge to enter into and exit from said recess;
  a piston return spring about said stem portion of said gas pressure piston, and bearing at one end on a head portion of said gas pressure piston;
  a multi-function spring member disposed to close an aft extent of said recess and to span a bore of said housing in which said gas pressure piston is received, said spring member including:
    a) an aft surface against which seats said return spring;
    b) a pair of axially and circumferentially extending spring fingers each engageable by an aft end surface of the injection cartridge, and said spring fingers both yielding to allow entry into said recess of said injection cartridge and latching of said latching lugs with said latching plate members, and upon unlatching of said injection cartridge said spring fingers at least partially ejecting said injection cartridge from said recess;
    c) a central guide hole slidably receiving a forward portion of said stem of said gas pressure piston and both guiding said stem relative to and aligning said stem with said injection cartridge; and
    d) a diametrically opposite pair of axially and radially extending spring arms each respectively engaging with one of said latching plate members to urge said latching plate members to a first position in which said latching plate members latchingly engage with said latching lugs of said injection cartridge, and said spring arms yielding to allow said latching plate members to slide laterally to a second position allowing said injection cartridge to move into and from said recess.

23. A gas powered hypodermic jet injection device, said device comprising:
  a device body having provision for engaging with and carrying a jet injection cartridge;
  said device body defining a gas piston bore into which is communicated pressurized gas to effect a jet injection;
  a gas piston reciprocable in said gas piston bore of said device body and cooperable with the jet injection cartridge to reciprocate in said gas piston bore so as to effect a jet injection in response to communication of pressurized gas to said gas piston bore and gas piston;
  a valve device for controllable effecting communication of pressurized gas from a source thereof to said gas piston bore and gas piston;
  said device body including a first portion and a second portion which comparably provide for carrying said injection cartridge, and which also carry said valve device and said source of pressurized gas for communication into said gas pressure bore and to said gas pressure piston, said first body portion and second body portion further comparably defining a joint line extending axially of said device body, with said first body portion and said second body portion each including provisions for securing to one another, and one of said first body portion and said second body portion defining a cylindrical extension extending axially and defining a through bore, said through bore of said one body portion sealingly and movably receiving said gas piston;
  wherein said device body further includes a laterally extending guide way disposed at one end of said bore and adjacent to said injection cartridge, said guide way providing for said device body to movably receive a pair of latching plates for lateral relative movement to latch with and unlatch from the injection cartridge, and said pair of latching plates being captively and movably received between said first body portion and said second body portion.

24. The jet injection device of claim 23 wherein in said device body further defines a laterally extending recess adjacent to and spaced toward said cylindrical body portion relative to said guide way, a plate-like spring member being received into said laterally extending recess and spanning a forward end of said bore.

25. The jet injection device of claim 24 wherein said one body portion defines a reduced diameter bore portion of said bore which reduced diameter bore portion is disposed at the aft end of said bore, said reduced diameter bore portion providing a step on said bore, and said reduced diameter bore portion being threaded to sealingly receive a stem member having a head disposed within said bore, so that said plate-like member and said head of said stem cooperatively capture said gas piston therebetween.

26. A gas powered hypodermic jet injection device, said device comprising:

a device body having provision for engaging with and carrying a jet injection cartridge;

said device body defining a gas piston bore into which is communicated pressurized gas to effect a jet injection;

a gas piston reciprocable in said gas piston bore of said device body and cooperable with the jet injection cartridge to reciprocate in said gas piston bore so as to effect a jet injection in response to communication of pressurized gas to said gas piston bore and gas piston;

a valve device for controllable effecting communication of pressurized gas from a source thereof to said gas piston bore and gas piston;

said device body including a first portion and a second portion which comparably provide for carrying said injection cartridge, and which also carry said valve device and said source of pressurized gas for communication into said gas pressure bore and to said gas pressure piston, said first body portion and second body portion further comparably defining a joint line extending axially of said device body, with said first body portion and said second body portion each including provisions for securing to one another and one of said first body portion and said second body portion defining a cylindrical extension extending axially and defining a through bore, said through bore of said one body portion sealingly and movably receiving said gas piston;

wherein said device body outwardly defines a pair of diametrically opposite and axially extending grooves each extending toward a forward end of said device body, each of said first body portion and said second body portion defining a respective one of said pair of grooves, and a trigger sleeve being axially slidably movable over said cylindrical extension, said trigger sleeve including a pair of diametrically opposite axial projections each extending toward a forward end of said device body, and said pair of axial projections of said trigger sleeve respectively being received slidably into said pair of axially extending grooves of said device body portions.

* * * * *